United States Patent [19]

Smirnov et al.

[11] 4,169,029
[45] Sep. 25, 1979

[54] METHOD FOR ELECTRICAL PURIFICATION AND DECONTAMINATION OF LIQUIDS AND APPARATUS FOR EFFECTING SAME

[75] Inventors: Oleg V. Smirnov; Vasily G. Kozhemyakin; Valentin I. Barabanov; Ivan S. Lavrov; Reald A. Okunev; Nikolai I. Rukobratsky, all of Leningrad, U.S.S.R.

[73] Assignee: Leningradsky Inzhenerno-Stroitelny Institut, Leningrad, U.S.S.R.

[21] Appl. No.: 513,132

[22] Filed: Oct. 8, 1974

[51] Int. Cl.² .......................... C02B 1/82; B03C 5/00
[52] U.S. Cl. .................................... 204/149; 204/152; 204/180 R; 204/272
[58] Field of Search .......... 204/149, 152, 131, 180 R, 204/272; 210/44

[56] References Cited

U.S. PATENT DOCUMENTS

| | | | |
|---|---|---|---|
| 398,101 | 2/1889 | Webster, Jr. | 204/149 |
| 672,231 | 4/1901 | Lacomme | 204/149 X |
| 2,955,076 | 10/1960 | Gossling | 204/131 X |
| 2,997,430 | 8/1961 | Foyn | 204/151 |
| 3,192,142 | 6/1965 | Vellas et al. | 204/149 X |
| 3,340,175 | 9/1967 | Mehl | 204/149 X |
| 3,468,778 | 9/1969 | Hirs et al. | 204/180 R |
| 3,725,226 | 4/1973 | Stoner | 204/149 |
| 3,843,507 | 10/1974 | Kwan | 204/149 X |

OTHER PUBLICATIONS

Pohl, "Non-Uniform Electric Fields", *Scien. Amer.*, vol. 203, No. 6, Dec. 1960, pp. 107–111.

*Primary Examiner*—Arthur C. Prescott
*Attorney, Agent, or Firm*—Holman & Stern

[57] ABSTRACT

A method for the electric purification and decontamination of liquids containing suspended and dissolved matter, such as mineral, organic and biological substances, comprises passing a pulsating electric current through a starting liquid, the current having sufficient pulse duration and voltage to cause electric discharge between the electrodes. An apparatus for realizing the method of electric purification and decontamination of liquids comprising a coagulation chamber with at least two rod-type electrodes electrically insulated by means of individual insulators from the housing of the coagulation chamber and mounted together with their insulators to execute reciprocal motion along their longitudinal axes.

7 Claims, 6 Drawing Figures

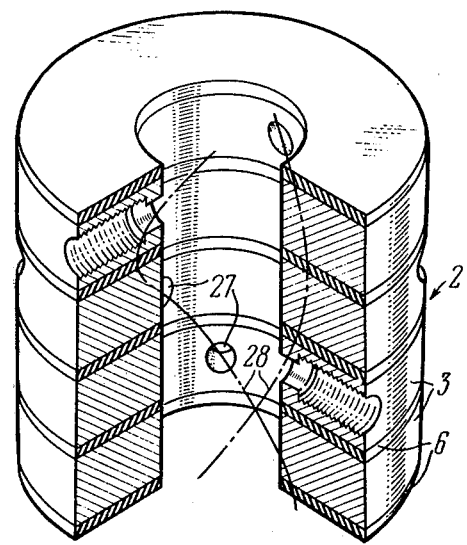
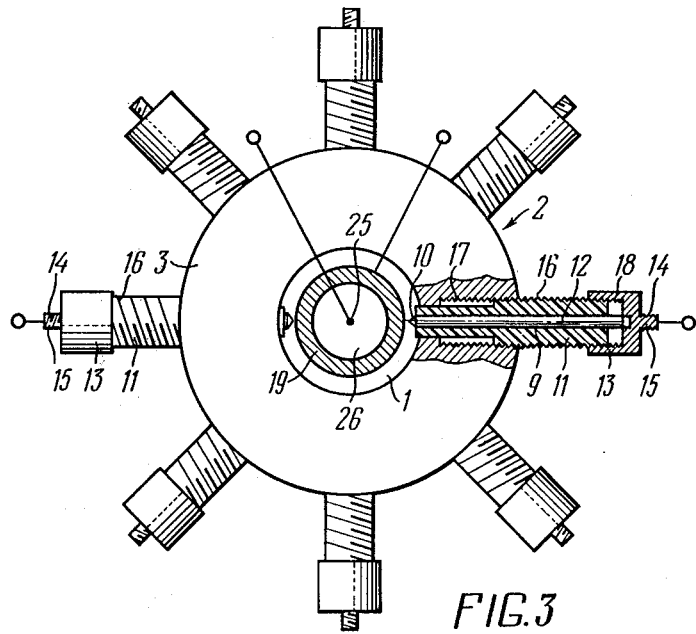

4,169,029

METHOD FOR ELECTRICAL PURIFICATION AND DECONTAMINATION OF LIQUIDS AND APPARATUS FOR EFFECTING SAME

ORIGIN OF THE INVENTION

The Government has rights in this invention pursuant to Grant CHE-11389 awarded by the National Science Foundation.

BACKGROUND OF THE INVENTION

The present invention relates to a method for the electrical purification and decontamination of liquids and to an apparatus for effecting same.

An apparatus according to the present invention can find application, in example, for supplying water to troops in the field, for supplying water to geological parties in remote regions, for supplying water to timber logging sites, radar stations, surface and sub-surface ships and other vessels, for supplying water to manned orbiting space stations; it can also be used in water preservation systems for the above-mentioned applications, as well as for the purification of water by removing radioactive and toxic substances in the chemical and chemico-pharmaceutical industry for the recovery of valuable substances, as well as for medico-biological purposes, such as preparation of pyrogenic water.

Known in the art is a method for the purification and decontamination of liquids a wherein the liquid is passed, sequentially or in parallel, through inter-electrode gaps formed by flat electrodes, with a constant or pulsating voltage in the range of from 3 to 30 volts.

Disadvantages of the above process resulting from a rather low field intensity, its uniformity and the quite character of the process hydrodynamics, reside in the deposition of an oxide film on the anode surface, the presence of a concentration polarization effect, deposit formation on the cathode, increasing equivalent resistance of the inter-electrode space, and the necessity of introducing an oxidizing agent to convert $Fe(OH)_2$ into $Fe(OH)_3$.

Another prior art method for the electric purification and decontamination of liquids comprises passing a liquid through a packed inter-electrode space, the packing being comprised of metal chips or other metal particles, arranged in layers separated from each other by porous diaphragms, the voltage across the electrodes being under 100 volts.

A disadvantage of the above-described method resides in that the porous diaphragm tends to become clogged with metal hydroxide due to a limited volume of flake removal, resulting in increased hydraulic resistance to the flow of liquid, with a considerable portion of the flow passing through the packing without taking part in the purification process, since the surfaces of the chips in the packing are in a state of mutual electrical contact.

According to another known method the liquid passes through the inter-electrode space formed by coaxially arranged cylinder electrodes, the voltage applied thereto being under 100 volts.

A disadvantage of the above method resides in low efficiency of dipolophoresis, due to low non-uniformity of the electric field another disadvantage is the decreasing efficiency of the process under increasing intensity of the electric field and concentration of suspended particles, due to intensive deposition of particles on the anode under the conditions of quiet hydrodynamics of the process.

Also known in the art is a method for the purification and decontamination of liquids by means of a high-voltage electric discharge wherein a liquid is subjected to the effect of electrical discharge, the voltage used being in the order of 10000–100000 volts, current over 100 amperes and pulse duration of from 0.1 to 100 microseconds, which results in heavy losses of electric power, the presence of reactance losses, unsatisfactory bactericidal effect, dangerous sounds, voltages and currents, as well as the formation of cancerogenic substances in the process of purification.

Also known in the art is an apparatus for effecting the purification and decontamination of liquids for realizing the first mentioned method, which apparatus comprises a coagulation chamber having electrodes in the form of flat plates. A disadvantage of the apparatus resides in a large anode surface and the impossibility of smooth adjustment of the inter-electrode space, which results in the formation of an oxide film on the surface of the anode, the appearance of concentration polarization, the formation of deposits on the cathode which increases equivalent resistance of the inter-electrode space, and the need to introduce an oxidizer for the purpose of converting $Fe(OH)_2$ into $Fe(OH)_3$.

The known apparatus for effecting the electric purification and decontamination of liquids realizing the above-mentioned method wherein packed electrodes are used in the form of a bank of cells separated from each other by porous diaphragms arranged between current-conducting electrodes, has disadvantages which reside in the fact that as the process proceeds the packed material tends to dissolve, which calls for the application of special devices for compressing the packed material and requires the current polarity to be changed.

There is also known an apparatus for realizing the above-mentioned method wherein use is made of cylindrical electrodes and the apparatus comprises a coagulation chamber with coaxial cylindrical electrodes.

A disadvantage of the apparatus resides in the fact that due to low non-uniformity of the electrical field of the inner large-diameter electrode, which reduces the value of dipolophoretic forces, independent of the charge of the particles, it is necessary to provide a presettler for removing large particles having a low electric charge.

There is also known an apparatus for the electric purification and decontamination of liquids for realizing the method and employing a high-voltage electrical discharge. In this apparatus the starting liquid flows through a coagulation chamber wherein at least two rod type electrodes are disposed, one of the rod-type electrodes is electrically insulated from the housing of the coagulation chamber by means of an insulator, the electrodes being disposed inside the housing in such a manner that their longitudinal axes lie in parallel planes, the distance between the planes being within the size of the inter-electrode space.

The electrodes in the apparatus are fixedly secured in the housing. Among the disadvantages of the apparatus are a large destruction of insulation of one of the electrodes, a low degree of utilization of the purification volume, the necessity of frequent replacement of one of the electrodes, and the need of having a very high-strength housing.

SUMMARY OF THE INVENTION

It is an object of the present invention to provide a method for the electric purification and decontamination of liquids, ensuring the removal of dissolved inorganic matter from the starting liquid.

Another object of the present invention is to provide a method for the electric purification and decontamination of liquids, ensuring the removal of dissolved organic matter from the starting liquid.

Still another object of the present invention is to provide a method for the electric purification and decontamination of liquids, permitting the removal of suspended inorganic matter from the starting liquid.

Yet another object of the present invention is to provide a method for the electric purification and decontamination of liquids, permitting the removal of suspended organic matter from the starting liquid.

A further object of the present invention is to provide a method for the electric purification and decontamination of liquids, permitting the removal of biological matter from the starting liquid, such as microorganisms, fungi and algae.

A still further object of the present invention is to provide an apparatus for the electric purification and decontamination of liquids to realize the proposed method and ensure the removal of dissolved matter from the starting liquid.

It is also an object of the present invention to provide an apparatus for the electric purification and decontamination of liquids for realizing the proposed method and ensuring the removal of suspended inorganic matter from the starting liquid.

It is also an object of the present invention to provide an apparatus for the electric purification and decontamination of liquids to realize the proposed method and ensure the removal of suspended organic matter from the starting liquid.

It is also an object of the present invention to provide an apparatus for the electric purification and decontamination of liquids to realize the proposed method and ensure the removal of suspended biological matter, such as microorganisms, from the starting liquid.

These and other objects of the present invention are achieved in a method for the electric purification and decontamination of liquids containing suspended and dissolved matter, such as mineral, organic and biological substances, by passing an electric current through the starting liquid by means of electrodes, wherein, according to the present invention, the current passed through the starting liquid is pulsating, the duration of pulses and the voltage being sufficient for ensuring the appearance of electric discharges between the electrodes.

The duration of the current pulses is advantageously selected to exceed 0.001 second, the voltage being from 100 to 6000 volts, while the distance between the electrodes is selected to be within the range of from 0.1 to 10 mm, depending on the physicochemical properties of the starting liquid.

These objects are achieved also in an apparatus for the electric purification and decontamination of liquids for realizing the method, comprising a coagulation chamber having at least two rod-type electrodes, one of the two electrodes being electrically insulated from the housing of the coagulation chamber by means of an insulator, the two electrodes being arranged in the housing in such a manner that their longitudinal axes are disposed in parallel planes, the distance between the planes being within the inter-electrode gap. The second rod-type electrode is also electrically insulated from the housing of the coagulation chamber by means of another insulator, both rod-type electrodes together with their respective insulators being mounted in the housing of the chamber and adapted to execute reciprocal motion along their longitudinal axes.

For the purpose of intensifying the removal of dissolved matter from the liquid and decontaminating the liquid, the coagulation chamber is preferably provided with an additional electrode in the form of a hollow rod for the treated liquid to flow therethrough, rotatably mounted inside the chamber substantially adjacent the butt end of the electrodes and adapted to execute reciprocal motion along the longitudinal axis of the chamber.

In order to provide for a dipolophoretic effect and ensure maximum non-uniformity of the electric field, an additional electrode in the form of a string, made of a metal which is insoluble in the starting liquid under the effect of electric current, is preferably arranged inside the additional electrode along the longitudinal axis thereof, the string electrode forming, in conjunction with the first-mentioned additional electrode, an additional coagulation chamber, such embodiment being conducive to the intensified recovery of highly dispersed impurities.

In another embodiment involving a plurality of rod-type electrodes, their continuous operating time is increased and operation facilitated by advantageously arranging the electrodes to be mounted at points spaced along a helical line inside the housing of the coagulation chamber.

The above-described embodiment of the apparatus for realizing the proposed method for the electric purification and decontamination of liquids offers the possibility of acting upon the physical and colloido-chemical properties of the purified liquid, thus decontaminating the starting liquid in which not only the vegetative form of bacteria, but also spore-forming species and bacteriophage are present, as well as to obtain irreversible coagulation aggregates containing $Fe(OH)_3$, which are formed bypassing the bivalent form and possess maximum absorbing surface.

BRIEF DESCRIPTION OF THE DRAWINGS

Other objects and advantages of the present invention will become apparent to those skilled in the art upon a further reading of this disclosure in which the preferred embodiments are set forth in detail in conjunction with the accompanying drawings, wherein

FIG. 2 presents an axonometric view of the housing of a coagulation chamber according to the present invention, showing the points whereat the electrodes are secured to the housing;

FIG. 3 shows a partially cut-away view along arrow A in FIG. 1;

DETAILED DESCRIPTION OF THE PREFERRED EMBODIMENT

Figure 1:
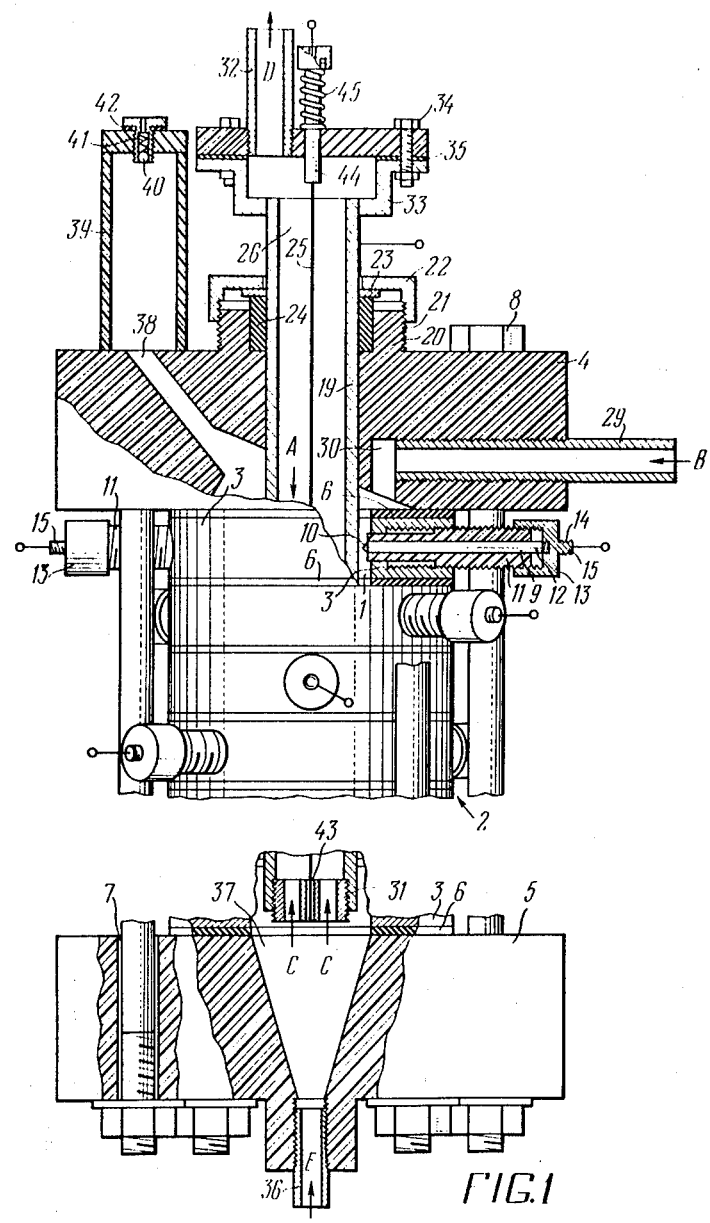
FIG. 1 illustrates an apparatus for the electric purification and decontamination of liquids, according to the invention, realizing the method for the invention (overall semisectional cut-away view)

The proposed method for the electric purification and decontamination of liquids containing suspended and dissolved matter, such as mineral, organic and/or biological substances, comprises passing a pulsating electric current through a starting liquid by means of electrodes, the duration of current pulses and the voltage being sufficient to cause the appearance of low-intensity electric discharges between the electrodes.

The current pulse duration is selected to exceed 0.001 second, and the voltage being in the range of from 100 to 6000 volts, and the distance between the electrodes being from 0.1 to 10 mm, depending on the physico-chemical properties of the starting liquid.

The preferred embodiment of the method for the electric purification and decontamination of liquids will be shown with reference being had to the examples of electric purification and decontamination of the following liquids: a true solution of an inorganic substance, namely, crystalline iodine; a true solution of an organic matter, namely, methylene blue; colloidodispersed systems, such as a suspension of Cambrian clay, marsh and river water (the Neva and Fontanka rivers), as well as water infested with bacteria, such as bacteria $E.\ Coli$ and Anthracis.

The method according to the present invention is illustrated below by detailed examples of the electric purification and decontamination of a crystalline iodine solution in a concentration of 200 mg/liter; a solution of methylene blue in a concentration of 6 to 70 mg/liter; a suspension of Cambrian clay in a concentration of 2.0 to 5000 mg/liter; marsh and river water having a turbidity index 2 to 250 mg/liter and a color index of 15 to 680 degrees, infested with bacteria $E.\ Coli$ in a concentration of from $10^2$ to $10^7$ cm$^{-3}$, and water infested with anthracis in a concentration of from $10^2$ to $10^7$ cm$^{-3}$.

EXAMPLE 1

To one group of electrodes intended for providing low intensity electric discharges, there was applied an electric voltage in the range of from 100 to 500 volts, the inter-electrode gap was from 0.1 to 0.6 mm, the duration of the non-flashover portion of the pulse was 0.002 second, the duration of the flashover pulse was 0.003 second, whereas to the other group of electrodes which were not creating low-intensity current discharges, there was applied a constant direct voltage of 40 volts and the starting liquid was passed through the inter-electrode space, the liquid in this case was a solution of crystalline iodine in a concentration of 200 mg per liter. The flow of the starting liquid was subjected to the combined action of the electric field created by the electrodes, the current pulses and the low-intensity electric current discharges.

Under the combined effect of thes factors the dissolved material was recovered in the form of coagulated particles.

After filtering through a foamed plastic filter, the concentration of iodine was 20 mg/liter.

EXAMPLE 2

Voltage in the range of from 600 to 1000 volts was impressed to the first group of electrodes, the inter-electrode gap was from 0.8 to 3.0 mm, the duration of the non-flashover portion of the pulse was 0.003 second, the duration of the flashover pulse was 0.002 second, whereas to the other group of electrodes a voltage of 40 volts was applied and a solution of crystalline iodine with a starting concentration of 200 mg/liter was passed through the chamber. The process of electric purification was carried out similarly to that described in Example 1.

After filtering through a foamed plastic filter, the iodine concentration was zero.

EXAMPLE 3

Voltage in the range of from 3000 to 6000 volts was applied to the first group of electrodes, the inter-electrode gap was from 6 to 10 mm, the duration of the non-flashover portion of the pulse was 0.003 second, the duration of the flashover pulse was 0.02 second. To the other group of electrodes a voltage of 40 volts was applied and a solution of methylene blue in a concentration of 6 mg/liter was passed through the chamber.

The process of electric purification was carried out similarly to that described in Example 1.

After filtering through a foamed plastic filter, the concentration of methylene blue was zero.

EXAMPLE 4

Voltage in the range of from 100 to 300 volts was applied to the first group of electrodes, the inter-electrode gap was from 0.1 to 0.6 mm, the duration of the non-flashover portion of the pulse was 0.003 second, the duration of the flashover pulse was 0.02 second. To the other group of electrodes a voltage of 40 volts was applied and a solution of methylene blue in a starting concentration of 6 mg/liter was passed through the chamber.

The process of electric purification was carried out similiarly to that described in Example 1.

After filtering through a foamed plastic filter, the concentration of methylene blue was 0.5 mg/liter.

EXAMPLE 5

Voltage in the range of from 600 to 1000 volts was applied to the first group of electrodes, the inter-electrode gap was from 0.8 to 3.0 mm., the duration of the non-flashover portion of the pulse was 0.004 second, the duration of the flashover pulse was 0.01 second. To the other group of electrodes a voltage of 40 volts was applied and a solution of methylene blue with a starting concentration of 6 mg/liter was passed through the chamber.

The process of electrical purification was carried out similarly to that described in Example 4.

After filtering through a foamed plastic filter, only traces of methylene blue could be found.

EXAMPLE 6

Voltage in the range of from 3000 to 6000 volts was applied to the first group of electrodes, the inter-electrode gap was from 6 to 10 mm., the duration of the non-flashover portion of the pulse was 0.008 second, the duration of the flashover pulse was 0.01 second. To the other group of electrodes a voltage of 40 volts was applied and a solution of methylene blue in a concentration of 70 mg/liter was passed through the chamber.

The process of electrical purification was carried out similarly to that described in Example 4.

After filtering through a foamed plastic filter, the concentration of methylene blue was 0.01 mg/liter.

EXAMPLE 7

Voltage in the range of from 100 to 300 volts was applied to the first group of electrodes, the inter-electrode gap was from 0.1 to 0.6 mm., the duration of the non-flashover portion of the pulse was 0.003 second, the duration of the flashover pulse was 0.002 second. To the other group of electrodes, a voltage of 40 volts was applied and a suspension of Cambrian clay in a starting concentration of 500 mg/liter was passed through the chamber.

The process of electric purification was carried out similarly to that described in Example 1. However, under the effect of the factors indicated in Example 1, the present Example was characterized by the coagulation of substantially suspended particles.

After filtering through a foamed plastic filter, the concentration of Cambrian clay was zero.

EXAMPLE 8

Voltage in the range of from 600 to 1000 volts was applied to the first group of electrodes, the inter-electrode gap was from 0.8 to 3.0 mm., the duration of the non-flashover portion of the pulse was 0.02 second, the duration of the flashover pulse was 0.003 second. To the other group of electrodes, a voltage of 40 volts was applied and a suspension of Cambrian clay in a concentration of 10 mg/liter was passed through the chamber.

The process of electric purification was carried out similarly to that described in Example 7.

After filtering through a foamed plastic filter, the concentration of Cambrian clay was zero.

EXAMPLE 9

Voltage in the range of from 3000 to 6000 volts was applied to the first group of electrodes, the inter-electrode gap was from 6 to 10 mm, the duration of the non-flashover portion of the pulse was 0.004 second, the duration of the flashover pulse was 0.01 second. To the other group of electrodes, a voltage of 40 volts was applied and a suspension of Cambrian clay in a starting concentration of 5000 mg/liter was passed through the chamber.

The process of electric purification was carried out similarly to that described in Example 7.

After filtering through a foamed plastic filter, the concentration of Cambrian clay was zero.

EXAMPLE 10

Voltage in the range of from 100 to 300 volts was applied to the first group of electrodes, the inter-electrode gap was from 0.1 to 0.6 mm, the duration of the non-flashover portion of the pulse was 0.002 second, the duration of the flashover pulse was 0.003 second. To the other group of electrodes, a voltage of 40 volts was applied and water with a turbidity of 20 mg/liter, a color index of 75 degrees, an odor index of 5 points and a taste index of 3 points, was passed through the chamber.

The process of electric purification was carried out similarly to that described in Examples 1 and 7.

After filtering through a foamed plastic filter, the water had a turbidity of 2 mg/liter, a color index of 12 degrees, an odor index of 3 points and a taste index of 2 points.

EXAMPLE 11

Voltage in the range of from 600 to 1000 volts was applied to the first group of electrodes, the inter-electrode gap was from 0.8 to 3.0 mm, the duration of the non-flashover portion of the pulse was 0.003 second, the duration of the flashover pulse was 0.005 second. To the other group of electrodes, a voltage of 40 volts was applied and water with a turbidity of 176 mg/liter, a color index of 300 degrees, an odor index of 5 points and a taste index of 3 points was passed through the chamber.

The process of electric purification was carried out similarly to that described in Examples 1 and 7.

EXAMPLE 12

Voltage in the range of from 3000 to 6000 volts was applied to the first group of electrodes, the inter-electrode gap was from 6 to 10 mm, the duration of the non-flashover portion of the pulse was 0.002 second, the duration of the flashover pulse was 0.08 second. To the other group of electrodes, a voltage of 40 volts was applied and water with a turbidity of 250 mg/liter, a color index of 490 degrees, an odor index of 5 points, and a taste index of 3 points was passed through the chamber.

The process of electric purification was similar to that described in Examples 1 and 7.

After filtering through a foamed plastic filter the water had a turbidity of 1 mg/liter, a color index of 4 degrees, a odor index of 1 point and a taste index of 1 point.

Table 1 below lists detailed data on the water characteristics prior to and following the process of electric purification.

Table 1

| Name 1 | Unit 2 | Starting water 3 | Treated water 4 | Standard values to USSR State Standards 5 |
|---|---|---|---|---|
| Lucidity | cm | 14 | 30 | at least 30 |
| Turbidity | mg/lit | 46 | 0.1 | under 2.0 |
| Color | degrees | 400 | 8–9 | under 20 |
| Odor | points | 5 | 1 | under 2 |
| Taste | points | 3 | 1 | under 2 |
| pH | | 6.86 | 7.16 | 6.5 to 9.5 |
| Oxidability (permanganate) | $mgO_2$/lit | 18.8 | 5.6 | unspecified |
| Total hardness | mg. eqv/lit | 2.2 | 1.4 | under 7 |
| Carbonates | mg. eqv/lit | 2.0 | 1.4 | unspecified |
| Non-carbonate hardness | mg. eqv/lit | 0.2 | 0 | unspecified |
| Cations | | | | |
| Calcium | mg/l | 42.0 | 24.0 | unspecified |
| Magnesium | mg/l | 1.0 | 0.4 | unspecified |
| Iron, bi-and trivalent | mg/l | 0 | 0 | under 0.3 |
| Ammonia | mg/l | 0.8 | 0.3 | unspecified |
| Potassium-Sodium | mg/l | 13.7 | 11.04 | unspecified |
| Anions | | | | |
| Chlorides | mg/l | 14.2 | 17.7 | unspecified |
| Sulphites | mg/l | 0 | 0 | unspecified |
| Hydrocarbonates | mg/l | 122.0 | 85.0 | unspecified |
| Nitrites | mg/l | 0.015 | 0.01 | unspecified |
| Nitrates | mg/l | 0 | 0 | unspecified |

EXAMPLE 13

Voltage in the range of from 100 to 300 volts was applied to the first group of electrodes, the inter-electrode gap was from 0.1 to 0.6 mm., the duration of the non-flashover portion of the pulse was 0.002 second, the duration of the flashover pulse was 0.003 second. To the other group of electrodes, a voltage of 40 volts applied and water infested with E. Coli having a starting concentration of bacteria of 7760 $cm^{-3}$ was passed through the chamber.

The process of electric purification was carried out similarly to that described in Examples 1 and 7. In this case, however, the electric discharges depressed the activity of the microorganisms and caused their destruction, thus resulting in the disinfection of the water.

After filtering through a foamed plastic filter, the concentration of microorganisms in the water was zero.

EXAMPLE 14

Voltage in the range of from 600 to 100 volts was applied to the first group of electrodes, the inter-electrode gap was from 0.8 to 3.0 mm, the duration of the non-flashover portion of the pulse was 0.003 second, the duration of the flashover pulse was 0.002 second. To the other group of electrodes, a voltage of 40 volts was applied and water infested with *E.Coli* in a concentration of microorganisms of 105333 $cm^{-3}$ was passed through the chamber. The process of electric purification was carried out similarly to that described in Example 13.

After filtering through a foamed plastic filter, the concentration of microorganisms was 8 $cm^{-3}$.

EXAMPLE 15

Voltage in the range of from 3000 to 6000 volts was applied to the first group of electrodes, the interelectrode gap was from 6 to 10 mm, the duration of the non-flashover portion of the pulse was 0.005 second, the duration of the flashover pulse was 0.8 second. To the other group of electrodes, a voltage of 40 volts was applied and water infested with *E.Coli* bacteria in a concentration of microorganisms of 4 000 000 $cm^{-3}$ was passed through the chamber.

The process of electric disinfection was carried out similarly to that described in Example 13.

After filtering through a foamed plastic filter, the concentration of microorganisms was zero.

EXAMPLE 16

Voltage in the range of from 100 to 300 volts was applied to the first group of electrodes, the inter-electrode gap was from 0.1 to 0.6 mm, the duration of the non-flashover portion of the pulse was 0.002 second, the duration of the flashover pulse was 0.003 second. To the other electrodes, a voltage of 40 volts was applied and water infested with anthracoid in a concentration of microorganisms in the order of 7000000 $cm^{-3}$ was passed through the chamber.

The process of electric disinfection was carried out similarly to that described in Example 13.

After filtering through a foamed plastic filter, the concentration of the microorganism was 6 $cm^{-3}$.

EXAMPLE 17

Voltage in the range of from 600 to 1000 volts was applied to the first group of electrodes, the inter-electrode gap was from 0.8 to 3.0 mm, the duration of the non-flashover portion of the pulse was 0.003 second, the duration of the flashover pulse was 0.01 second. To the other group of electrodes, a voltage of 40 volts was applied and water infested with anthracoid, having a starting concentration of microorganisms of 700000 $cm^{-3}$ was passed through the chamber.

The process of electric disinfection was carried out similarly to that described in Example 13.

After filtering through a foamed plastic filter, the concentration of microorganisms was zero.

EXAMPLE 18

Voltage in the range of from 3000 to 6000 volts was applied to the first group of electrodes, the inter-electrode gap was from 6 to 10 mm, the duration of the non-flashover portion of the pulse was 0.004 second, the duration of the flashover pulse was 0.08 second. To the other group of electrodes, a voltage of 40 volts was applied and water infested with anthracoid in a starting concentration of microorganisms of 105600000 $cm^{-3}$ was passed through the chamber.

The process of electric disinfection was carried out similarly to that described in Example 13.

After filtering through a foamed plastic filter, the concentration of the microorganisms was zero.

The apparatus for the electric purification and decontamination of liquids for realizing the above-described method comprises, according to the invention, a main chamber 1 (FIG. 1) for coagulation through which chamber the liquid to be purified and disinfected is to flow.

A cylindrical housing 2 of the chamber 1 comprises four metal washers 3 (FIGS. 1 and 2), spaced apart and separated from top 4 (FIG. 1) and bottom 5 covers of the housing 2 by dielectric gaskets 6 (FIGS. 1 and 2).

The top cover 4 and the bottom cover 5 (FIG. 1) have apertures 7 accommodating bolts 8, the bolts tighten the washers 3 of the housing 2.

The coagulation chamber 1 has eight main rod-type electrodes 9 with tapered ends 10, the electrodes are electrically insulated from the washers 3 of the housing 2 of the chamber 1 by means of individual insulators 11. The rod-type electrodes 9 are mounted inside the housing 2 in such a manner that their longitudinal axes 12 lie in parallel planes, the distance between the planes being within the width of the inter-electrode gap, which in this case is from 0.1 to 10 mm.

Electric current is applied to the rod-type electrodes 9 (FIGS. 1 and 3) from an independent power source, conventionally shown in the drawings by current-conducting bushings 13 which are connected to the electrodes 9 and have an external thread 14 on their shank portions 15.

The rod-type electrodes 9, together with their respective insulators 11, are secured in the washers 3 of the housing 2 of the chamber 1, being adapted to execute reciprocal motion along their longitudinal axes 2 through a distance, insuring the inter-electrode gap of from 0.1 to 10 mm. For this purpose the insulators 11 (FIG. 3) are provided with an external thread 16 adapted to engage a thread 17 in the washer 3 to be translated thereby together with the rod-type electrodes 9, whereas the bushings 13 are provided with an inner thread 18, ensuring the displacement of the bushings along the thread 16 together with the electrodes 9. Such an embodiment of the insulators 11 of the electrodes 9 offers a very compact design of the apparatus. The above embodiment also permits the period of continuous operation of the apparatus to be increased as the electrodes 9 are consumed.

The coagulation chamber 1 (FIG. 1) is also provided with an additional electrode 19 embodied in the form of a hollow cylindrical rod through which the liquid to be treated is intended to flow. The electrode 19 (FIGS. 1 and 3) is arranged inside the chamber 1 in direct proximity to the butt ends 10 of the main rod-type electrodes 9. The electrode 19 extends outside through the top cover 4 (FIG. 1).

The electrode 19 is made of iron or other erodable material and is also rotatably mounted and adapted to execute reciprocal axial motion along the longitudinal axis of the chamber 1. To this end, a projection 20 in the top cover 4 is provided with a thread 21 accommodating a nut 22 with a washer 23 and a sealing gasket 24 which embrace the electrode 19. The feature residing in the fact that the electrode 19 is rotatably arranged with a provision for reciprocal motion along the longitudinal axis of the chamber 1, is conductive to an even and uniform dissolution (erosion) of the portions of the surface of the electrode 19 which are opposite the butt ends 10 of the main electrodes 9, the erosion assuming the form of a groove circumferentially encompassing the electrode 19, which forms on the new surface of the electrode 19 every time the latter performs reciprocal motion.

Inside the additional electrode 19 there is provided longitudinally thereof another additional electrode 25, embodied in the form of a string made of a metal that is insoluble in the starting liquid under the effect of electric current, which metal in the present case is nickel. The electric current is fed to the electrodes 19 and 25 from the same source that is adapted to feed the electrodes 9.

The additional electrode 25, together with the additional electrode 19, form an additional coagulation chamber 26, which feature permits the process to be intensified due to the dipolophoretic forces of a non-uniform electric field which appears as the liquid flows through the additional coagulation chamber 26, the forces acting upon the molecules and suspended particles of inorganic, organic and biological matter.

Points 27 (FIG. 2) at which the rod-type electrodes 9 (FIG. 1) are secured in the washers 3 (FIG. 2) of the housing 2, are arranged along two helical lines 28 on the housing 2, which embodiment is conducive to a more ordered liquid flow, permits the service life of the additional electrode 19 to be increased due to its more uniform erosion, and facilitates the adjustment of the inter-electrode gap.

A connection 29 in the top cover 4 together with a channel 30 serve for the delivery of the starting liquid into the coagulation chamber 1 in the direction indicated by the arrow B (FIG. 1). A union 31 serves for delivering the liquid treated in the coagulation chamber 1 to the coagulation chamber 26, in the direction indicated by the arrows C. The treated liquid is discharged from the coagulation chamber 26 via an outlet union 32 secured in the funnel portion 33 of the electrode 19 by means of bolts 34 and sealed with a gasket 35. The starting liquid can also be fed in the direction indicated by the arrow E into both chambers 1 and 26 via a union 36 fitted in the bottom cover 5.

The sediment accumulating in the channel 37 in the process of coagulation is removed from the channel 37 as the starting liquid is admitted through the connection 29 and discharged through the union 32, for which purpose the union 36 is unscrewed and the sediment drained.

Cases accumulating in the process of coagulation are discharged from the coagulation chamber 1 via a channel 38, a pipe connection 39 and a discharge valve 40, the latter being spring-loaded with a spring 41 and sealed with gasket 42.

The additional electrode 25 in the form of a string is secured on the one end in central channel 43 of the union 31 and on the other end in a finger 44, extending through the side plate and loaded with a spring 45.

Figure 4:
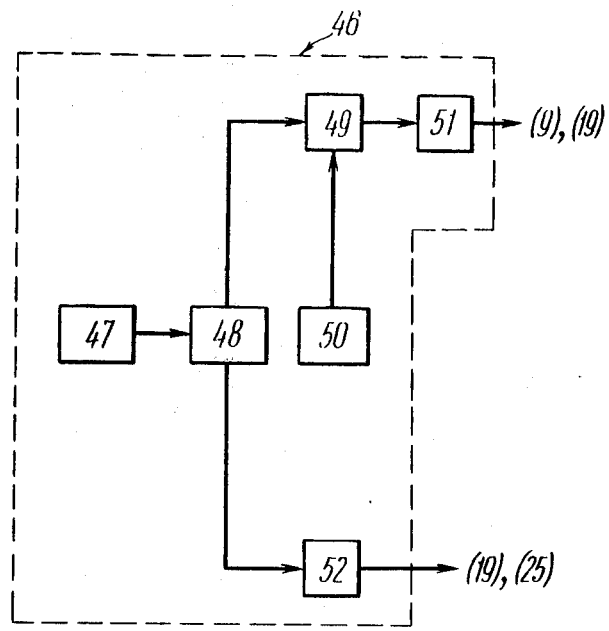
FIG. 4 illustrates the block diagram of a power pack of the proposed apparatus.

The main rod-type electrodes 9 (FIG. 1), the additional electrode 19 and the additional electrode 25 are all connected to an independent power source 46 (FIG. 4), which in FIGS. 1 and 3 is shown conventionally. The latter comprises an adjustable source 47 of alternating current to which a transformer 48 is connected. To the transformer 48 there is connected a controlled gate 49 coupled to a phase-shift string 50 which form, in combination, a pulse shaper to preset a certain pulse duration. To the controlled gate 49 there is connected a means 51, which means serves for restricting the current when the electric charge develops into an electric arc, the means 51 being connected in series to the main rod-type electrodes 9 and the additional electrode 19. The transformer 48 is also connected to a gate 52, the latter being connected to the additional electrodes 19 and 25.

Figure 5:
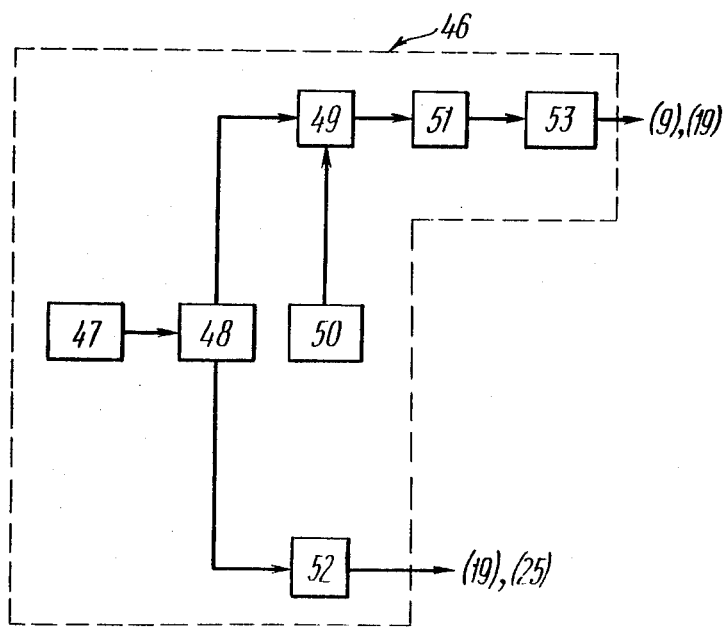
FIG. 5 is another embodiment of the power pack shown in FIG. 4.

In another embodiment of the independent power source 46 (FIG. 5), a pulse distributor 53 is connected to the means 51 for restricting the current as the electric discharge develops into an electric arc and series-connected to the main rod-type electrodes 9 and the additional electrode 19. The pulse distributor 53 is built around transistors.

Figure 6:
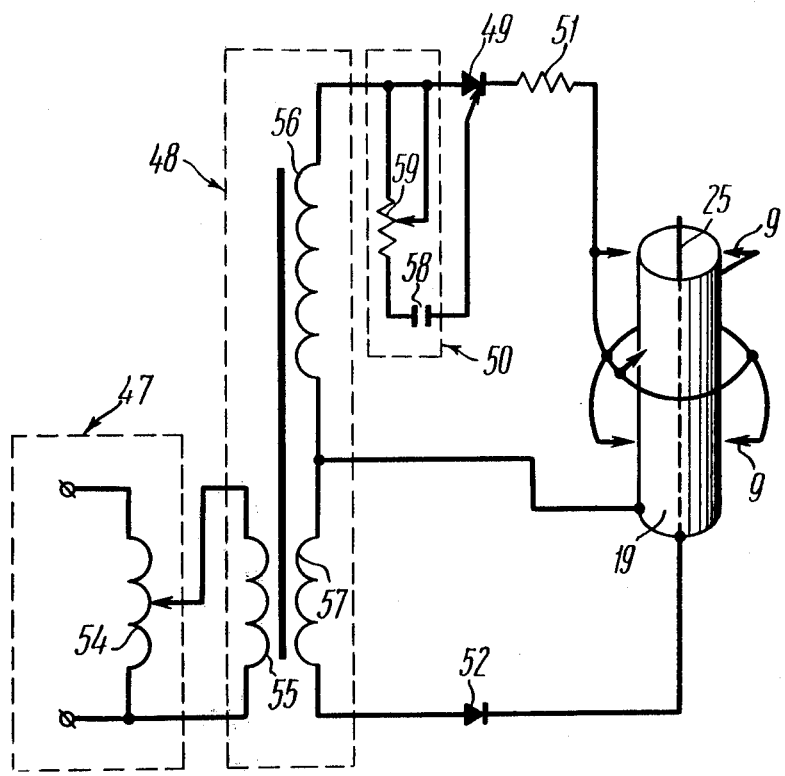
FIG. 6 is the elementary diagram of the independent power source shown in FIG. 4.

In the elementary diagram of the independent power source 46 (FIG. 4) illustrated in FIG. 6, the source of alternating current 47 is made as a winding 54, permitting an adjustable voltage to be obtained which is further applied across a primary winding 55 of the transformer 48, the latter having two output windings 56 and 57, for high voltage in the order of from 100 to 6000 volts and for low voltage in the order of from 0 to 100 volts, respectively. The high voltage winding 56 is connected to the controlled gate 49 and the low voltage winding 57 is connected to the gate 52.

The controlled gate 49 is embodied as a thyristor and the gate 52 is a diode. The phase-shift string 50 comprises a capacitor 58 and a variable resistor 59. The means 51 for restricting the value of current is made as a resistor.

We have described hereinabove an embodiment of the coagulation chamber 1 comprising eight main central electrodes 9. Another embodiment, however, is possible, wherein the chamber is provided with two rod-type electrodes, in case the volume of liquid to be treated is small. In case of weakly contaminated liquids, another embodiment of the apparatus is advantageous, wherein there is contemplated only one coagulation chamber 1, without the additional electrodes 19 and 25 which form the additional coagulation chamber 26. The number of rod-type electrodes can be increased, both within the body of one washer, for example all four pairs of electrodes can be disposed in one washer, one over the other, or the number of washers can also be increased in case large volumes of liquid are to be electrically purified and decontaminated.

In the described embodiment of the apparatus the additional electrode 19 is made in the form of a hollow cylinder rod, however, those skilled in the art will readily appreciate that the hollow electrode can be embodied with a surface other than cylindrical.

The apparatus according to the present invention operates similarly for all the above-mentioned starting liquids and the operation is carried out in accordance with the modes described in the above examples.

The operating principle of the apparatus according to the invention for the electrical purification and decontamination of liquids, realizing the method of the present invention, is as follows.

Current flows between the rod-type electrodes 9 (FIG. 1) and the additional electrode 19, the current pulsating with a pulse duration and a voltage which are sufficient to cause the appearance of electric discharges between the electrodes. In order to correlate the active period of the electric field of the main rod-type electrodes 9 and the additional electrode 19 with the relaxation time and the course of colloido-chemical processes in the starting liquid, the pulse duration is selected to be greater than 0.001 second, the voltage is selected to be within the range of from 100 to 6000 volts and the distance between the electrodes 9 and the electrode 19 is selected to be in the interval from 0.1 to 10 mm depending on the physiochemical properties of the starting liquid.

Then the starting liquid is fed via the connection 29 and the channel 30 to the coagulation chamber 1 in the direction of the arrow B.

The small intensity electrical discharges forming between the electrodes 9 and 19 in the coagulation chamber 1 cause the appearance of coagulation centers with the help of instantly originating particles of $Fe(OH)_3$ and suppress the vital activity of microorganisms. The partially coagulated inorganic and organic particles enter the coagulation chamber 26, moving in the direction of the arrows C, and in passing between the electrodes 25 and 19 concentrate in the zone of maximum non-uniformity of the electric field at the electrode 25 where they irreversibly aggregate, this aggregation is aided by the acidic-alkaline gradient along the radius of the chamber 26.

Then the liquid is delivered along the arrow D to a foamed plastic filter (not shown in the drawings) and therefrom to the consumer.

During the passage of the liquid through the main coagulation chamber 1, the main rod-type electrodes 9 (FIG. 1) arranged circumferentially along the helical lines 28 (FIG. 2) encourage the breaking up of the liquid flow and uniform mixture of the products of electrical purification, rendering the latter more effective.

As the proposed apparatus operates, the main rod-type electrodes 9 will erode, consequently, in the course of time the inter-electrode gap must be adjusted by turning the insulator 11, whereas a finer adjustment of the inter-electrode gap is achieved by turning the current-conducting bushings 13.

In case the main rod-type electrodes 9 need to be reciprocally displaced through larger distances, they are moved by turning the insulators 11 (coarse adjustment) and then by turning the bushings 13 (fine adjustment). When one or more main rod-type electrodes 9 erode so must that neither of the adjustments is capable of ensuring the desired inter-electrode gap and further operation of the apparatus is impossible, the electrodes 9 are replaced by unscrewing the bushings 13 and removing the spent electrodes 9. Similar replacement is performed when it is desired to insert an electrode 9 made of another material. As the outer surface of the additional electrode 19 becomes eroded, the electrode is turned around its axis, whereas it is longitudinally displaced if a circular groove appears on its surface, the displacement being achieved by releasing the nut 22. After the additional electrode 19 is set in the desired position, the nut 22 is tightened again.

In case the output of the apparatus cannot be adjusted to any tangible degree, it is expedient to install a smaller number of washers 3 and a larger number of main rod-type electrodes 9. The output of the apparatus can be increased by removing the bolts 8, removing the top cover 4 or the bottom cover 5 and fitting the required number of washers 3. Thereafter the bolts 8 are set in place and tightened again.

As described above, the apparatus according to the invention operates in such a manner that the starting liquid is fed along the arrow B, through the connection 29 and the channel 30 to the coagulation chamber 1, in which chamber, the effect of a non-uniform electric field of the main rod-type electrodes 9 causes the appearance of dipolophoretic and ponderomotive forces acting on the molecules and particles in the suspension as well as on the gas bubbles, resulting in their coagulation as well as flocculation under the action of the hydroxide of the electrode material which forms in the process. All these factors tend to intensify the process of electric purification. Then the liquid flows in the direction of the arrows C into the additional coagulation chamber 26, wherein under the effect of the forces of a non-uniform electric field, which are mainly dipolophoretic, created by the inner surface of the additional electrode 19 and the additional electrode 25, the particles contained in the liquid will additionally reversibly coagulate; the particles are further transported to the additional electrode 25, concentrate around it and irreversibly coagulate, which process yields easily separated dense irreversible floccules at the outlet of the outlet union 32. The treated liquid, as described above, flows from the outlet union 32 in the direction indicated by the arrow D.

Another sequence of treatment of the starting liquid is also possible, specifically in case the treated suspension has a simple composition. In this case, as indicated above, the liquid enters through the union 36 simultaneously into both chambers 1 and 26.

It is readily apparent that the process of electric purification can also be carried out by using only the main coagulation chamber 1, without the additional coagulation chamber 26, which is advantageous in performing the electric purification of slightly contaminated, mainly biologically contaminated liquids.

The present invention, realizing the method and the apparatus for the electric purification and decontamination of liquids also comprises such as treatment of the liquid which induces therein physicochemical and colloido-dispersion processes to considerably improve the quality of the treated liquid since the time of the pulse action corresponds to the time of relaxation processes in the liquid.

The method and the apparatus according to the invention permit such operations as purchasing, storage and batching of reagents to be dispersed with. The method, while involving low electric power consumption in the order of from 0.1 to 1 kWt/hr per cubic meter of the starting liquid, together with small overall dimensions of the apparatus, which is about 800×600×400 mm for the output in the order of from 10 to 25 cubic meters per day, will produce a highly effective purification and decontamination of waters which can hardly be purified by conventional methods. Water treated by the proposed method realized by the apparatus according to the invention in the opinion of specialists tastes like spring water.

What is claimed is:

1. A method for the electric purification and decontamination of liquids containing suspended and dissolved matter, comprising the step of: passing a pulsating electric current by means of electrodes through a starting liquid, the duration of the current pulses being in the range of from 0.001 to 0.805 second, the voltage being in the range of from 100 to 6000 volts and the distance between the electrodes being from 0.1 to 10 mm., sufficient to cause electric discharges between the electrodes.

2. An apparatus for the electrical purification and decontamination of liquids containing suspended and dissolved matter, by passing a pulsating electric current through a starting liquid, comprising in combination: a coagulation chamber having an inlet and an outlet for the starting liquid; a housing of the coagulation chamber; at least two rod-type electrodes made of an erodible metal mounted in the housing of the coagulation chamber in such a manner that the longitudinal axes thereof lie in parallel planes, the distance between the planes being within the inter-electrode gap; at least two separate individual insulators, the number thereof corresponding to the number of the rod-type electrodes, the insulators being intended for providing electrical insulation of the rod-type electrodes from the housing of the coagulation chamber; the rod-type electrodes together with their respective insulators being mounted in the housing of the coagulation chamber to execute reciprocal motion along their respective longitudinal axes through a preset distance; a power source for supplying the rod-type electrodes, electrically connected to the electrodes to apply thereto the pulsating electric current; a means provided in the coagulation chamber for removing gases accumulating in the coagulation chamber in the process of electric purification and decontamination of the starting liquid.

3. The apparatus as claimed in claim 2, further comprising: a plurality of the rod-type electrodes; the rod-type electrodes being mounted in the housing of the coagulation chamber at points arranged along at least one helical line on the housing.

4. An apparatus for the electric purification and decontamination of liquids containing suspended and dissolved matter, by passing a pulsating electric current through a starting liquid, comprising in combination: a coagulation chamber having an inlet and an outlet for the starting liquid to flow therethrough; a housing of the coagulation chamber; at least two rod-type electrodes made of an erodible metal mounted in the housing of the coagulation chamber in such a manner that their respective longitudinal axis lie in parallel planes, the distance between the parallel planes being within the inter-electrode gap; at least two individual insulators, the number thereof corresponding to the number of the rod-type electrodes, the insulators being intended to ensure electric insulation of the rod type electrodes from the housing of the coagulation chamber; the rod-type electrodes together with their respective insulators being mounted in the housing of the coagulation chamber to execute reciprocal motion along their respective longitudinal axes; an electrode in the form of a hollow rod and made of an erodible metal also included in the coagulation chamber; the electrode in the form of a hollow rod, intended to ensure the passage of the starting liquid therethrough, the outlet of the electrode in the form of a hollow rod being the outlet of the coagulation chamber; the electrode in the form of a hollow rod mounted in direct proximity to the butt ends of the rod-type electrodes and being adapted to execute rotary motion and reciprocal motion along the longitudinal axis of the coagulation chamber; the rod-type electrodes adapted to be displaced in the direction of the electrode in the form of a hollow rod through a distance of from 0.1 to 10 mm.; an electric power source electrically connected to each respective one of the electrodes for supplying thereto a pulsating electric current with the current pulse duration exceeding 0.001 second, the voltage being in the range of from 100 to 6000 volts, to ensure the appearance of electrical discharge between each of the rod-type electrodes and the electrode in the form of a hollow rod, to carry out the process of electric purification and decontamination of the starting liquid and for disinfection thereof; a means provided in the housing of the coagulation chamber for removing gases accumulating in the coagulation chamber in the process of electric purification and decontamination of the starting liquid.

5. The apparatus as claimed in claim 4, further comprising: a plurality of the rod-type electrodes; the points for mounting the rod-type electrodes in the housing of the coagulation chamber being arranged along at least one helical line on the housing.

6. The apparatus as claim in claim 4, further comprising: an electrode in the form of a string disposed inside the electrode in the form of a hollow rod along the longitudinal axis thereof; the electrode in the form of a string, made of a metal which is insoluble in the starting liquid under the action of electric current; the electrode in the form of a string forming together with the electrode in the form of a hollow rod another coagulation chamber; the electrode in the form of a string electrically connected to the power source.

7. The apparatus as claimed in claim 6, further comprising: a plurality of the rod-type electrodes being mounted in the housing of the first coagulation chamber at points arranged along at least one helical line on the housing.

* * * * *